United States Patent [19]

Wolak

[11] Patent Number: 4,836,226
[45] Date of Patent: Jun. 6, 1989

[54] ENDLESS ARTICLE FOR CLEANING TEETH

[76] Inventor: Ronald G. Wolak, 221 Parkland, Rochester Hills, Mich. 48063

[21] Appl. No.: 123,558

[22] Filed: Nov. 20, 1987

[51] Int. Cl.⁴ .............................................. A61C 15/00
[52] U.S. Cl. .................................... 132/321; 132/328
[58] Field of Search .................. 132/89, 93, 90, 91, 132/321–383; 433/3

[56] References Cited

U.S. PATENT DOCUMENTS

| | | | |
|---|---|---|---|
| 1,832,604 | 11/1931 | Wupper | 132/93 |
| 1,839,486 | 1/1932 | Lawton | 132/93 |
| 2,821,202 | 1/1958 | Davis | 132/93 |
| 3,141,466 | 7/1964 | Fleming | 132/93 |
| 3,491,776 | 1/1970 | Fleming | 132/89 |
| 3,511,249 | 5/1970 | Baitz | 132/89 |
| 3,699,979 | 10/1972 | Muhler et al. | 132/89 |
| 3,800,812 | 4/1974 | Jaffe | 132/89 |
| 4,315,517 | 2/1982 | Krag | 132/89 |
| 4,326,547 | 4/1982 | Verplank | 132/89 |
| 4,364,380 | 12/1982 | Lewis | 132/91 |
| 4,414,990 | 11/1983 | Yost | 132/91 |
| 4,450,849 | 5/1984 | Cerceo et al. | 132/89 |
| 4,523,600 | 6/1985 | Donovan | 132/89 |
| 4,550,741 | 11/1985 | Krag | 132/89 |

FOREIGN PATENT DOCUMENTS 8100959 4/1981 PCT Int'l Appl. ............... 132/93

*Primary Examiner*—Paul J. Hirsch
*Attorney, Agent, or Firm*—Brooks & Kushman

[57] ABSTRACT

An endless article (10) for cleaning between teeth is disclosed as including a first segment (18) of an elastic material and also a second segment (20) of an inelastic material bonded together by their ends to form the endless article (10). The endless article (10) includes a directionally effective abrasive surface (14) and is graspable by a pair of hands. The article (10) is stretchable for proportionately reducing the cross section of the first segment (18) to position a section thereof between the teeth. A section of the article (10) is movable thereafter along its longitudinal axis (L) between the teeth for cleaning there-between.

18 Claims, 2 Drawing Sheets

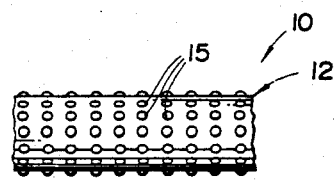
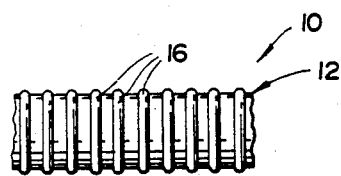
Fig. 5　　　　　Fig. 6
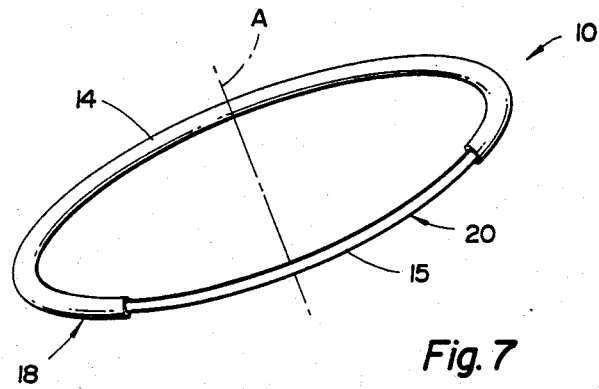
Fig. 7
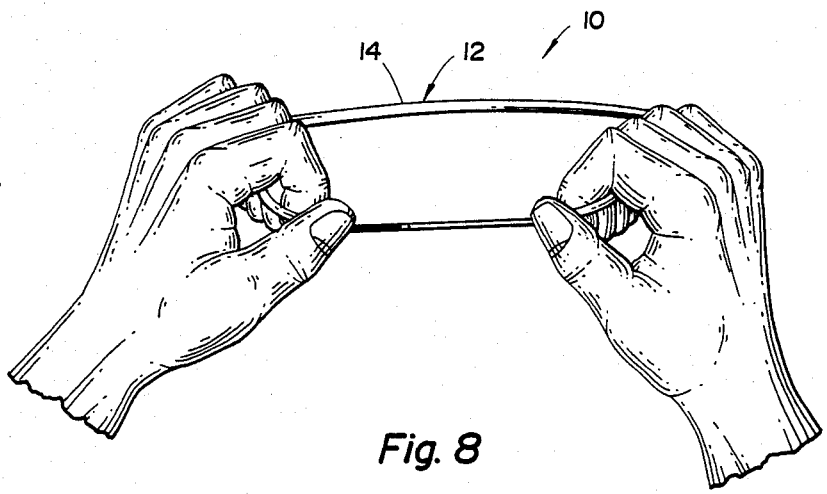
Fig. 8

ENDLESS ARTICLE FOR CLEANING TEETH

TECHNICAL FIELD

This invention relates to an endless article of a two piece construction for use in cleaning the spaces between human teeth.

BACKGROUND ART

Dental floss is widely used to clean and remove food, plaque and tartar build-up from between teeth. Conventional dental floss comprises a filament of a deformable or non-deformable material that is insertible between human teeth thereby to allow for cleaning of the teeth when the floss is moved along the teeth surfaces.

Problems arise in handling and operating the filaments. Conventional filaments are secured for use by wrapping a number of windings of the filaments around a finger of each hand of a user. The filament is then stretched and inserted between the teeth of the user for cleaning. Convention dental floss cuts off circulation in the fingers that the filament is wrapped around and also causes discomfort for the user. The closest prior art appears to be a conventional rubber band.

DISCLOSURE OF THE INVENTION

An object of the present invention is to provide an endless article for dislodging residual food particles, cleaning away plaque, and removing tartar from between teeth that is economical to manufacture, easy to use and that eliminates the strangulation effect on fingers associated with conventional dental floss.

In carrying out the above object and other objects of the invention, an endless article for cleaning spaces between human teeth comprises an endless segment of an elastic material and having a uniform cross section. The endless segment has a directionally effective abrasive surface and is graspable by a pair of hands. The article is stretchable between a relaxed position and a stretched position for positioning a section thereof between the teeth. The article is thereafter movable between the teeth for cleaning proximal areas and also repositionable in the hands to allow an unused section to be used for cleaning after a used section becomes soiled or worn out.

In one embodiment of the invention the cross section of the article is proportionately reducible as the article is stretched for facilitating positioning of the article between the teeth. As the article is relaxed the pre-stretched cross section shape returns. In the preferred construction of the first embodiment, the article includes a coating to reduce resistance when positioning the article between the teeth. Preferably the coating is a wax or TEFLON, although other coatings are contemplated for use with the invention.

In a second embodiment of the invention, the article includes a first segment of an elastic material having the same limitations as the article constructed in accordance with the first embodiment. The article of the second embodiment also includes a second segment of a non-elastic material with ends bonded to the ends of the first segment to form the endless article. The second segment is comprised of a material selected from the group consisting of KEVLAR, nylon, polyester, TEFLON, GIRTEX or silicon and is made as a very fine filament that facilitates placement of the article between closely spaced teeth.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIG. 5 is an exploded view of a portion of the article illustrated as having an arrayed dimpled surface;

FIG. 6 is an exploded view of a portion of the article illustrated as having a ribbed surface;

FIG. 7 is a perspective view of the endless article constructed in accordance with the present invention and illustrated as a second embodiment having a two part construction wherein the two parts are bonded together; and FIG. 8 is an illustration of the article grasped by a user for use.

BEST MODE FOR CARRYING OUT THE INVENTION

Figure 1:
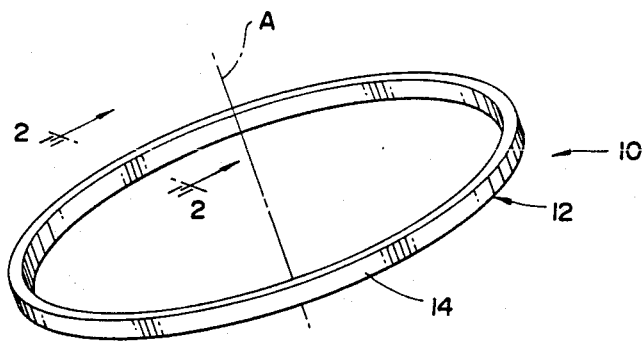
FIG. 1 is a perspective view of an endless article for cleaning between teeth constructed in accordance with the present invention and illustrated as a first embodiment and shown here as having a rectangular cross section.

Referring to FIG. 1 of the drawings, an endless article constructed in accordance with the present invention is generally indicated by reference numeral 10 and is used for dislodging residual food particles, cleaning away plaque and removing tartar from between teeth. As is hereinafter more fully described, the article 10 provides a substitute for conventional dental floss that is economical to manufacture, effective for cleaning spaces between teeth and avoids strangulation of fingers.

As shown in FIG. 1, the article 10 comprises an endless segment 12 of an elastic material and having a uniform cross section. Viewing FIG. 1 in conjunction with FIGS. 5 and 6, the segment 12 has a directionally effective abrasive surface 14 and is graspable by a pair of hands, shown in FIG. 8. The article 10 is stretchable between a relaxed position and a stretched position for positioning a section thereof between human teeth. The article 10 is movable between the teeth for cleaning between the teeth and is also repositionable in the hands to allow an unused section to be used for cleaning after a used section becomes soiled or worn out.

Referring to FIGS. 1 through 6 of the drawings, the cross section of article 10 is proportionately reducible as the article is stretched for facilitating positioning of the article between the teeth. As the positioned article 10 is relaxed, the cross section of the pre-stretched article is approached assuring effective contact of the abrasive surface 14 of the article with surfaces of the teeth.

Figure 2:
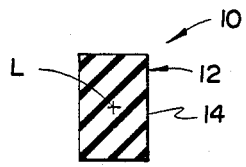
FIG. 2 is a sectional view taken along the lines 2—2 of FIG. 1 showing the rectangular cross section of the article.

FIGS. 1 and 2 illustrate the first embodiment of the endless article 10 wherein the cross section is generally rectangular in shape. Preferably the rectangular cross section is generally $\frac{1}{4}$ inch by 1/32 inch.

Figure 3:
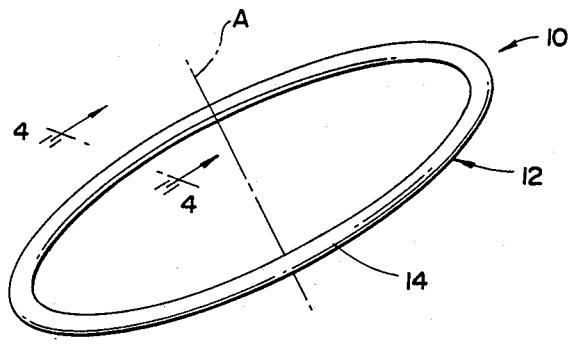
FIG. 3 is a perspective view of the first embodiment of the article illustrated as having a circular cross section.
Figure 4:
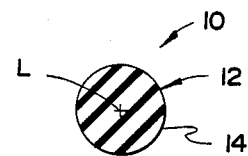
FIG. 4 is a sectional view taking along the lines 4—4 in FIG. 3 illustrating the circular cross sectional shape of the article.

FIGS. 3 and 4 illustrate the first embodiment of the endless article 10 wherein the cross section is generally circular in shape. Preferably the circular cross section is generally in the range from about 1/32 inch to about ⅛ inch in diameter.

Preferably, the article 10 in FIGS. 1 and 3 has a circumference in the range of about 3 to about 9 inches. An article 10 of this size is easy to use and store. Article 10 with larger circumferences are also as effective although the longer length is not required.

FIGS. 5 and 6 illustrate the directionally effective abrasive surface 14 of the article 10. In FIG. 5, the abrasive surface 19 comprises arrayed dimples 15 and in FIG. 6 the abrasive surface comprises ribs 16. Dimples 15 and ribs 16 can be independent and applied to segment 12 or formed as an integral part of the article 10. The placement of the dimples 15 and ribs 16 illustrated on article 10, in a generally linear fashion forming rows essentially parallel to the axis A of the article, allow the article to be easily positioned between the teeth in a direction of movement generally parallel to the axis A of the article yet provide abrasion for cleaning as a section of the article is moved along its longitudinal axis (L).

The article 10 shown in FIGS. 1 4 includes a coating 17 to reduce resistance when positioning the article between the teeth. The coating 17 is applied by any conventional means. Preferably the coating 17 is a wax or TEFLON which exhibits good lubricative properties although other coatings that provide a similar lubricative effect may be used.

In FIG. 7 a second embodiment of the invention is illustrated where the article 10 includes a first segment 18 of an elastic material having a uniform cross section and also includes a second segment 20 of an non-elastic material. The first segment 20 is constructed in accordance with the elastic construction of the heretofore described first embodiment of the invention.

Preferably article 10 constructed as the second embodiment also has a circumference generally in the range of about 3 to about 9 inches although the article may be a larger endless article.

With further reference to FIG. 7, the first segment 18 and second segment 20 are illustrated as being bonded together by their ends to form the endless article 10. Bonding is accomplished by any suitable chemical or mechanical bonding technique including but not limited to applying an adhesive. Tying the two segments 18,20 together is also contemplated. Preferably the first segment 18 is in the range of about ½ to about ¾ of the article 10 and respectively the second segment 20 is in the range of about ½ to about ¼ of the article.

Preferably, the second segment 20 is nonelastic and made from KEVLAR, nylon polyester, TEFLON, GIRTEX, or silicon. This second segment 20 is stronger and more cut resistant than the first segment 20. The second segment 20 preferably has a circular cross-section of a diameter typically smaller than that of the first segment 18 and is used for positioning between and cleaning teeth that are extremely close together.

FIG. 8 illustrates the positioning of the article 10 in the hands of the user in a use position. The article 10 is grasped with both hands with fingers wrapped around and through the center of the article 10. The article 10 is stretched when the hands are pulled apart. Forefingers of each hand are then used to position a short tightly stretched section of the article 10 in the mouth of the user between the teeth. The article 10 can be rotated in the hands of the user after each space between two teeth is cleaned to reduce wear on any one section and to provide an unused clean section for cleaning the next space.

While the best mode for carrying out the invention has been described in detail, those familiar with the art to which this invention relates will recognize various alternative designs and embodiments for practicing the invention as defined by the following claims.

What is claimed is:

1. An endless article (10) for cleaning between teeth, comprising: an endless segment (12) of an elastic material and having a generally uniform cross section; said segment (12) having a directionally effective abrasive cleaning surface (14) including dimples forming rows (15) situated essentially perpendicular to the circumference of the article (10) to allow the article to be easily inserted between the teeth, said dimples also forming rows situated parallel to the circumference of the article to provide abrasion for cleaning as a section of the article is moved parallel to its circumference; said article (10) being graspable by a pair of hands; said article (10) being stretchable between a relaxed position and a stretched position for positioning a section thereof between the teeth; said cross section being proportionately reducible in area as the article (10) is stretched for facilitating positioning of the segment between the teeth; said cross section also being returnable to the relaxed position size as the article (10) is relaxed, said article (10) being movable between the teeth for cleaning proximal areas and also being repositionable in the hands to allow an unused section to be used for cleaning after a used section of the directionally effective abrasive cleaning surface becomes soiled or worn out.

2. An endless article (10) as in claim 1 wherein said segment (12) includes a coating (17) to reduce resistance and facilitate sliding the article (10) into a use position between the teeth.

3. An endless article (10) as in claim 2 wherein said coating (17) is a wax.

4. An endless article (10) as in claim 2 wherein said coating (17) is TEFLON.

5. An endless article (10) as in claim 1 wherein said article (10) includes a first segment (18) and also including a second segment (20) with ends bonded to the ends of the first segment (18) to form the endless article (10).

6. An endless article (10) as in claim 5 wherein said first segment (18) is of an elastic material and having a uniform cross section; said cross section being proportionately reducible in area as the article (10) is stretched and also being returnable to the relaxed position size as the article (10) is relaxed.

7. An endless article (10) as in claim 6 wherein said second segment (20) is an inelastic material selected from the group consisting of KEVLAR, nylon, polyester, TEFLON, GIRTEX and silicon, said second segment being a fine filament for fitting between closely spaced teeth.

8. An endless article (10) as in claim 7 further including a coating (17) to reduce resistance and facilitate positioning of the article (10) between the teeth.

9. An endless article (10) as in claim 8 wherein said coating (17) is a wax.

10. An endless article (10) as in claim 8 wherein said coating (17) is TEFLON.

11. An endless article (10) as in claim 1 wherein the generally uniform cross section is generally rectangular in shape.

12. An endless article (10) as in claim 1 wherein the uniform cross section is generally elliptical in shape.

13. An endless article (10) as in claim 11 wherein the generally rectangular cross section is about ¼ of an inch by about 1/32 of an inch.

14. An endless article (10) as in claim 12 wherein the major axis of the elliptical section is about ¼ of an inch and the minor axis of the elliptical section is about 1/32 of an inch.

15. An endless article (10) as in claim 1 having a circumference in the range of about 3 to about 9 inches.

16. An endless article (10) of the type used to clean between teeth, characterized by an endless article (10) including first and second segments (18,20) bonded one to another by their ends, the first segment (18) being of an elastic material of a uniform cross section, the second segment (20) being of an inelastic material, said first segment (18) having a directionally effective abrasive surface (14) comprising dimples forming rows (15) situated essentially perpendicular to the circumference of the article (10) to allow the article (10) to be easily positioned between the teeth in a direction of movement generally perpendicular to the circumference of the article (10), said dimples also forming rows situated parallel to the circumference of the article (10) to provide abrasion for cleaning as a section of the article (10) is moved parallel to its circumference.

17. An endless article (10) of the type used to clean between teeth characterized by an endless article (10) including first and second segments (18,20) bonded to one another by their ends, the first segment being of an elastic material of a uniform cross section, the second segment (20) being of an inelastic material, said first segment (18) having a directionally effective abrasive surface (14) including ribs forming raised protuberances to allow the article to be easily positioned between the teeth yet provide abrasion for cleaning as a section of the article is moved parallel to its circumference.

18. An endless article (10) as in claim 17 wherein said ribs are oriented perpendicular to the circumference of the endless article (10).

* * * * *